United States Patent
Hara et al.

(10) Patent No.: US 10,327,623 B2
(45) Date of Patent: Jun. 25, 2019

(54) ENDOSCOPE CONNECTOR, ENDOSCOPE, AND ENDOSCOPE SYSTEM

(71) Applicant: FUJIFILM Corporation, Tokyo (JP)

(72) Inventors: Kazuyoshi Hara, Kanagawa (JP); Kimitake Fukushima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 305 days.

(21) Appl. No.: 15/409,540

(22) Filed: Jan. 19, 2017

(65) Prior Publication Data
US 2017/0202437 A1    Jul. 20, 2017

(30) Foreign Application Priority Data
Jan. 20, 2016    (JP) .................................. 2016-008569

(51) Int. Cl.
| A61B 1/00 | (2006.01) |
| A61B 1/05 | (2006.01) |
| A61B 1/12 | (2006.01) |

(52) U.S. Cl.
CPC ...... *A61B 1/00126* (2013.01); *A61B 1/00013* (2013.01); *A61B 1/00124* (2013.01); *A61B 1/00165* (2013.01); *A61B 1/05* (2013.01); *A61B 1/126* (2013.01)

(58) Field of Classification Search
CPC ............ A61B 1/00126; A61B 1/00013; A61B 1/00165; A61B 1/05; A61B 1/00114; A61B 1/00117; A61B 1/00124; A61B 1/00128
See application file for complete search history.

(56) References Cited

U.S. PATENT DOCUMENTS

| 8,088,064 | B2 | 1/2012 | Itoi | |
| 2006/0069307 | A1* | 3/2006 | Boulais | A61B 1/00128 600/132 |
| 2010/0305400 | A1* | 12/2010 | Onoda | A61B 1/00062 600/104 |
| 2012/0202385 | A1* | 8/2012 | Miyagi | A61B 1/00124 439/626 |

FOREIGN PATENT DOCUMENTS

JP    2008-093113    4/2008

* cited by examiner

*Primary Examiner* — Timothy J Neal
(74) *Attorney, Agent, or Firm* — JCIPRNET

(57) ABSTRACT

The invention provides an endoscope connector capable of stably performing image communication, an endoscope including the endoscope connector and endoscope system. An endoscope connector is provided in an endoscope having an imaging unit at a distal end of an insertion portion, connected with an endoscope processor device, and provided with an image signal transmitting unit transmitting an image signal with respect to the endoscope processor device via optical communication. The image signal transmitting unit is arranged in an image signal transmitting connector connected with a processor device connector. The image signal transmitting connector includes a glass member provided at the tip end through which the image signal passes and a guide member formed on a circumference of the glass member. The guide member has grooves thereon radially extending from the glass member.

11 Claims, 7 Drawing Sheets

ENDOSCOPE CONNECTOR, ENDOSCOPE, AND ENDOSCOPE SYSTEM

CROSS-REFERENCE TO RELATED APPLICATIONS

The present application claims priority under 35 U.S.C. § 119 to Japanese Patent Application No. 2016-008569, filed on Jan. 20, 2016. The above application is hereby expressly incorporated by reference, in its entirety, into the present application.

BACKGROUND OF THE INVENTION

Field of the Invention

The present invention relates to an endoscope connector, an endoscope, and an endoscope system, and particularly relates to an endoscope connector, an endoscope, and an endoscope system which transmit signals by way of optical communication.

Description of the Related Art

An endoscope system includes an endoscope and an endoscope processor device. The endoscope includes an imaging unit for taking an image in a body cavity such as a CCD (Charge Coupled Device) image sensor and a connector attached to the endoscope processor device, and the endoscope processor device includes a connector to which the connector of the endoscope is detachably attached, a controlling unit for subjecting image data output from the endoscope to image processing or the like, and a light source. In the endoscope system, the connector of the endoscope is connected with the connector of the endoscope processor device at an electric contact to supply electric power from the endoscope processor device to the endoscope, and transmit an image signal or a control signal between the endoscope processor device and the endoscope.

Image communication is attained by providing an LD (laser diode) element on the endoscope side and a PD (Photodiode) element on the endoscope system side, for example. The LD element is fixed with high accuracy to an axis called a LD guide, and the PD element is fixed with high accuracy to a hole into which the LD guide is inserted.

When the endoscope is connected with the endoscope system, the LD guide is inserted into the hole to which the PD element is fixed, and the image communication becomes possible between the endoscope and the endoscope system. In the endoscope system, the endoscope after use needs to be cleaned and sterilized, and if the cleaning and sterilizing causes water droplets to be present on a window glass part of the connector on the endoscope side, efficiency of a laser for the image communication decreases to possibly cause the image to be disturbed. If a tip end of the connector, that is, the window glass part, has a structure where the water droplets are likely to collect, dirt such as water scale accumulates to constitute a factor which deteriorates the laser efficiency.

Further, the LD guide for transmitting and receiving the image signal has a tip end with a tapered shape so as not to impair insertability thereof. The tapered shape of the LD guide has been a structure in which water droplets are likely to remain on the tip end surface at an inflection point between a tip end surface and tapered portion of the LD guide due to the pinning effect of wetting. The window glass part and the tip end of the LD guide are constructed so that the window glass part is concave (recessed or dented) as compared to the tip end of the LD guide in order to prevent the window glass part from being damaged. The window glass part made to be concave as compared to the tip end of the LD guide causes the water to be likely to collect at this concave portion, having resulted in the structure in which the water is less likely to escape and water droplets and dirt are likely to collect in the window glass part.

For example, as an endoscope device which ensures that the connectors of the endoscope and a control device are connected with each other and has a high watertight performance, Japanese Patent Application Laid-Open No. 2008-93113 describes an endoscope device in which a connector cover is slidable.

SUMMARY OF THE INVENTION

However, the endoscope device described in Japanese Patent Application Laid-Open No. 2008-93113 relates to a technology for making the connector watertight on the control device side, but does not consider the connector on the endoscope side. Therefore, it still cannot resolve the problem that the window glass part becomes dirty owing to water droplets or water scale after cleaning and sterilizing the window glass part of the connector on the endoscope side.

The present invention has been made in consideration such a circumstance, and aims to provide an endoscope connector which has a window glass part for performing image communication structured so that water droplets and dirt are less likely to collect and can stably perform image communication, and an endoscope and endoscope system including this endoscope connector.

In order to achieve the above object, the present invention provides an endoscope connector which is provided in an endoscope having an imaging unit at a distal end of an insertion portion, connected with a processor device connector of an endoscope processor device, and includes an image signal transmitting unit which transmits an image signal to the endoscope processor device via optical communication, wherein the image signal transmitting unit is arranged in an image signal transmitting connector which is to be connected with the processor device connector, the image signal transmitting connector includes: a glass member which is provided at a tip end thereof, through which the image signal passes; and a guide member formed on a circumference of the glass member, and the guide member has grooves thereon radially extending from the glass member.

According to the endoscope connector of the present invention, because the guide member included in the image signal transmitting connector has the grooves radially extending from the glass member, it is possible to easily eliminate water droplets adhered to the glass member with the groove. Therefore, water droplets adhered to the tip end of the image signal transmitting connector by cleaning, sterilizing or the like, can be moved from the glass member to the guide member and it is possible to prevent water droplets and dirt such as water scale from adhering to the glass member, and prevent a laser efficiency from decreasing.

In another aspect of the present invention, it is preferable that the glass member is concave from (dented from) the tip end of the image signal transmitting connector in a range equal to or less than 0.3 mm from the guide member.

According to this aspect, the glass member is made to be concave from the tip end of the image signal transmitting connector in a range equal to or less than 0.3 mm from the guide member, preventing the glass member from being damaged. Therefore, the laser efficiency can be prevented from decreasing. A level difference is formed by making the glass member to be concave from the guide member, and it may be possible that water droplets are likely to collect at this level difference, but in the present invention, the guide member has the grooves and the grooves can make water droplets be likely moved, and thus, water droplets do not collect and can be moved even if the level difference is provided.

In another aspect of the present invention, it is preferable that the grooves are formed in four to eight directions from the glass member at equal intervals between the grooves.

According to this aspect, the grooves are formed with the number of directions of four to eight at equal intervals from the glass member, allowing any of the formed grooves to be arranged in a gravitational direction in cleaning and sterilizing, even in a case where the image signal transmitting connector and the endoscope connector are fitted to each other with a screw structure when connecting the image signal transmitting connector to the endoscope connector. Therefore, water droplets can be easily eliminated via the grooves from the glass member.

In another aspect of the present invention, it is preferable that a corner formed by a bottom surface and lateral surface of the groove is C chamfered (chamfer plane) or round chamfered.

According to this aspect, the corner formed by the bottom surface and lateral surface of the groove is C chamfered or round chamfered, allowing dirt adhered to a groove portion to be easily removed.

In another aspect of the present invention, it is preferable that the guide member is round chamfered from the tip end of the image signal transmitting connector toward a circumference thereof.

According to this aspect, because the guide member is round chamfered from the tip end of the image signal transmitting connector toward the circumference, it is possible to eliminate an inflection point between the tip end and its lateral portion of the image signal transmitting connector. Therefore, water droplets adhered to the glass member can be likely moved to the guide member. By round chamfering the guide member, insertability of the endoscope connector can be ensured.

In another aspect of the present invention, it is preferable that a tip end of the guide member has a curved convex shape.

According to this aspect, because the tip end of the guide member is provided with the curved convex shape, the convex shape can prevent the glass member from being damaged even if the glass member is not made to be concave from (with respect to) the guide member. The glass member is configured so as not to be concave from the guide member and no level difference is present between the glass member and the guide member. Thus, it is possible to prevent the wiping article from being caught on between the glass member and the guide member and efficiently wipe the glass member when wiping the glass member using a wiping article of gauze or the like.

In another aspect of the present invention, it is preferable that the glass member has been subjected to a process for lowering adhering force of water.

According to this aspect, because the glass member has been subjected to the process for lowering the adhering force of water, allowing the water adhered to the glass member to be likely moved to the guide member.

In another aspect of the present invention, it is preferable that the process for lowering the adhering force of water is a process for subjecting the glass member to fluorine coating.

According to this aspect, the glass member is subjected to fluorine coating, allowing the adhering force of water on the glass surface to be lowered.

In another aspect of the present invention, it is preferable that a material of the glass member is sapphire glass.

According to this aspect, the glass member is made of sapphire glass, allowing the adhering force of water on the glass surface to be lowered.

In order to achieve the above object, the present invention provides an endoscope including: an imaging unit arranged at a distal end part thereof; a light guide which transmits a light to the distal end part; and the endoscope connector described above.

According to the endoscope of the present invention, since the endoscope includes the endoscope connector described above, the laser efficiency of transmitting the image signal is not lowered, allowing the image acquired by the imaging unit to be observed with high accuracy.

In order to achieve the above object, the present invention provides an endoscope system including: the endoscope described above; and an endoscope processor device including a light source which feeds a light to the light guide, a controlling unit which controls communication of an image signal, and a processor device connector which is connected with the endoscope connector and performs image signal communication via optical communication with the endoscope.

According to the endoscope system of the present invention, since it includes the endoscope described above, the laser efficiency of transmitting the image signal is not lowered, allowing the image acquired by the imaging unit to be observed with high accuracy.

According to the endoscope connector of the present invention, in the guide member included in the image signal transmitting connector in which the image signal transmitting unit is arranged, there are provided the grooves radially extending from the glass member arranged thereon. Thus, it is possible to easily eliminate water droplets adhered to the glass member from the groove. Therefore, it is possible to prevent the laser efficiency decrease caused by water droplets or dirt such as water scale.

By using the endoscope connector according to the present invention for the endoscope and the endoscope system, the image signal communication can be performed without decreasing the laser efficiency, allowing the image imaged by the imaging unit to be processed with high accuracy.

DETAILED DESCRIPTION OF THE PREFERRED EMBODIMENTS

Hereinafter, a description is given of an endoscope connector, an endoscope, and an endoscope system according to the present invention with reference to the attached drawings. In the description, the word "to" is used to mean that numerals before and after "to" are included as a lower limit and an upper limit.

Figure 1:
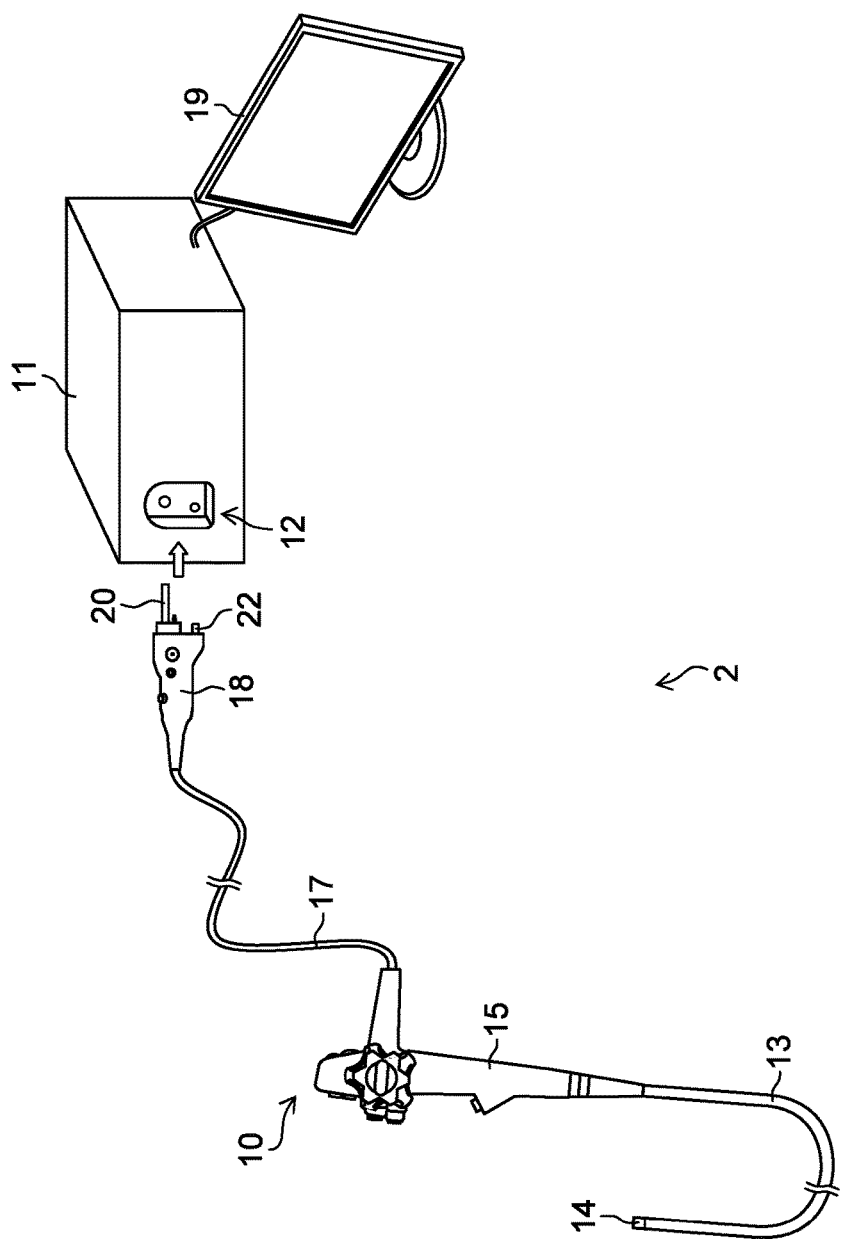
FIG. 1 is an outer appearance view showing an endoscope system.

FIG. 1 is an outer appearance view showing an endoscope system to which the present invention is applied. As shown in FIG. 1, an endoscope system 2 includes an endoscope 10, and an endoscope processor device (processor device for endoscope) 11.

The endoscope 10, which is illustrated as a flexible scope, has a flexible insertion portion 13 to be inserted in a body cavity of a patient, an operating portion 15 joined to a proximal end part of the insertion portion 13, a universal cord 17 joined to the operating portion 15, and an endoscope connector (connector for endoscope) 18 provided at an end of the universal cord 17 and connected to a processor device connector (connector for processor device) 12 of the endoscope processor device 11. However, the endoscope 10 is not limited to the flexible scope, and the present invention may also be applied to another type of endoscope such as a rigid scope.

A distal end surface of the insertion portion 13 is provided with an observation window, an illumination window and the like. In a distal end part 14 constituting a distal end of the insertion portion 13, there are arranged an objective optical system which forms an image, as an optical image, of an object light from an observed site taken in from the observation window, an imaging unit which converts the optical image image-formed by the objective optical system into an electrical signal, and the like.

The image signal output from the imaging unit is transmitted to an image signal transmitting unit 42 via a transmission cable which is arranged to be inserted through insides of the insertion portion 13, the operating portion 15, and the universal cord 17 to the endoscope connector 18. The image signal is converted into an optical signal by the image signal transmitting unit 42 and optically transmitted to the endoscope processor device 11 in a non-contact manner.

In the distal end part 14, there are also arranged a light emitting unit of a light guide which transmits a light for illuminating the observed site from the illumination window. The light guide is arranged to be inserted through the insides of the insertion portion 13, the operating portion 15, and the universal cord 17 to the endoscope connector 18. An image signal transmitting connector 22 and a light guide bar 20 linked to the light guide project from the endoscope connector 18.

The operating portion 15 is provided with an angle knob which adjusts an orientation of a distal end surface of the insertion portion 13 to upward, downward, rightward and leftward directions, an air and water feeding button for ejecting air and water from the distal end surface of the insertion portion 13, a release button for recording an endoscope image as a still image, and the like. The orientation of the distal end surface of the insertion portion 13 is adjusted by bending a bending portion which is provided adjacent to a proximal end side of the distal end part 14.

The universal cord 17 is covered by a tubular elongated outer wall having flexibility, and has an in-tube space inside the outer wall where the above signal cable, light guide, air and water feeding tube and the like are arranged to be inserted through hollow potions of the inside of the insertion portion 13 and the inside of the operating portion 15.

Figure 2:
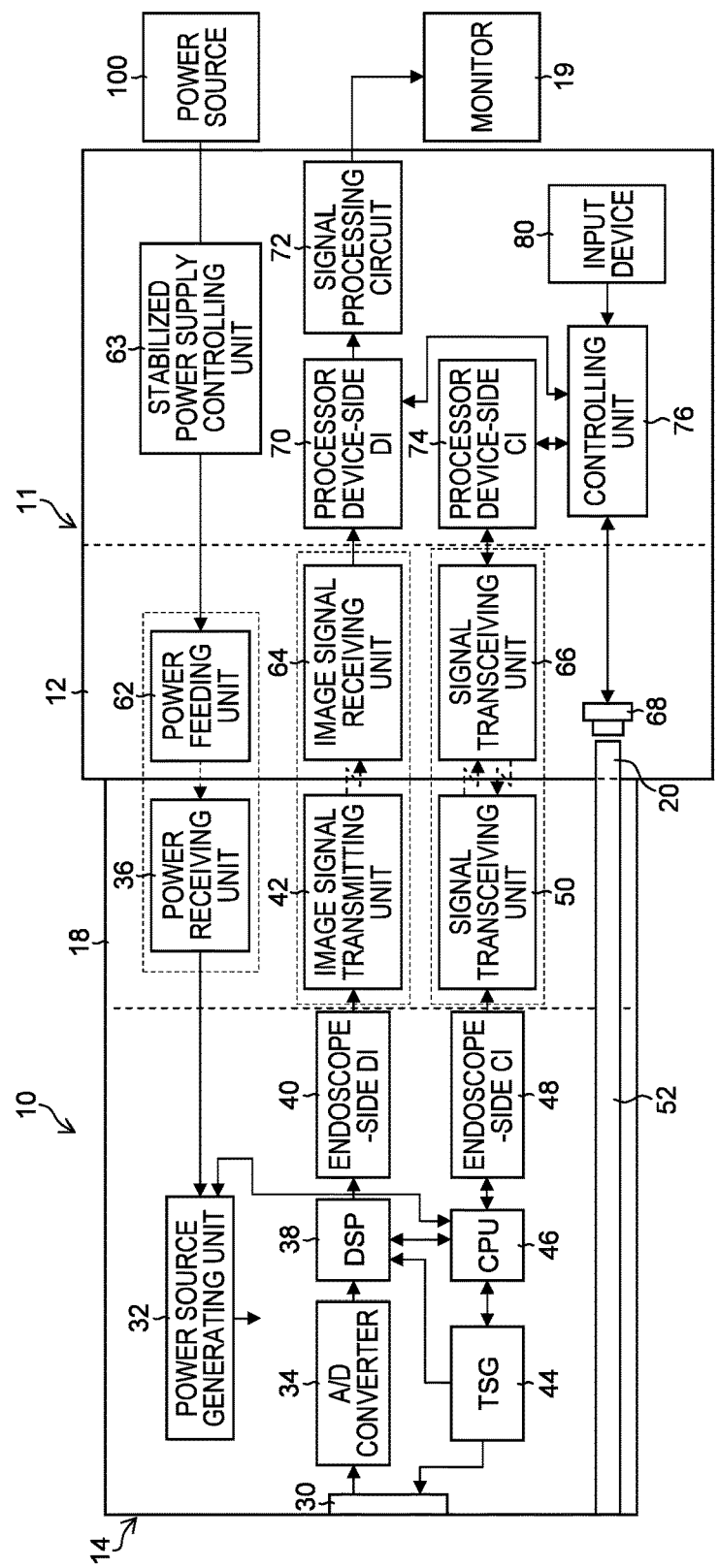
FIG. 2 is a block diagram showing a configuration of the endoscope system.

FIG. 2 is a block diagram showing a configuration of the endoscope system 2 shown in FIG. 1.

The endoscope connector 18 is connected with the processor device connector 12 of the endoscope processor device 11. The reception and feed of the electric power, the transmission and reception of the image signal, and the transmission and reception of the control signal are performed in a non-contact manner between the endoscope 10 and the endoscope processor device 11 via the endoscope connector 18 and the processor device connector 12. For this reason, the endoscope connector 18 has arranged therein, as described later, a power receiving unit 36 which receives the power in a non-contact manner, the image signal transmitting unit 42 which optically transmits non-contactually the image signal of the imaging unit 30, and an endoscope-side control signal transceiving unit (endoscope-side control signal transmitting and receiving unit) 50 which optically transceives (transmits and receives) non-contactually the control signal for controlling the imaging unit 30.

The endoscope processor device 11 is provided with the processor device connector 12. As described above, the endoscope connector 18 of the endoscope 10 is connected with the processor device connector 12 of the endoscope processor device 11. The endoscope processor device 11 supplies the electric power to the endoscope 10 (power feeding), and transceives the various signals to and from the endoscope 10.

The endoscope processor device 11 is provided with a light source. A light from the light source is supplied via the light guide bar 20 to the light guide and the light is transmitted from the light guide to the distal end part 14.

The endoscope processor device 11 includes a controlling unit 76 for controlling control signal communication and image signal communication.

The processor device connector 12 connected with the endoscope connector 18 has arranged therein a power feeding unit 62 which feeds the electric power to the power receiving unit 36 of the endoscope 10 in a non-contact manner, the image signal receiving unit 64 which receives the signal from the image signal transmitting unit 42 of the endoscope 10, and a processor device-side signal transceiving unit 66 which transceives the signal from an endoscope-side signal transceiving unit 50 of the endoscope 10.

The endoscope processor device 11 is provided with input devices (such as an operation switch, a keyboard, and a mouse) which are not shown in the figure. The endoscope system 2 entirely is generally controlled in accordance with an operation input from the input device by an operator.

Further, the endoscope processor device 11 takes in the image signal output from the imaging unit 30 in the distal end part 14 of the endoscope 10 and subjects the taken image signal to various signal processes to generate the image data for establishing a video (moving picture image) or still picture image of the observed site. Then, the generated image data is output to a monitor 19 connected through a cable to display the image or the like of the observed site on the monitor 19. The generated image data is recorded on a recording medium as needed.

The endoscope 10 is detachably attached (connected) by way of the endoscope connector 18 to the processor device connector 12 of the endoscope processor device 11. In the endoscope system 2 in the embodiment, the endoscope connector 18 of the endoscope 10 is attached to the processor device connector 12 of the endoscope processor device 11, through which an internal circuit in the endoscope 10 is connected with an internal circuit in the endoscope processor device 11 via a non-contact type device such as transformer or photocoupler. This ensures insulation between the internal circuit in the endoscope 10 and the internal circuit in the endoscope processor device 11. In other words, the configuration is made to be capable of achieving the control signal communication, the reception and feed of the power, and the image signal communication in a non-contact manner.

The electric power required for driving the internal circuit in the endoscope 10 is supplied from the endoscope processor device 11 by a non-contact power supply device which includes a power feeding unit 62 in the endoscope processor device 11 and a power receiving unit 36 in the endoscope 10. The power receiving unit 36 is arranged in the endoscope connector 18 of the endoscope 10, and the power feeding unit 62 is arranged in the processor device connector 12 of the endoscope processor device 11.

The non-contact power supply device is a device which transmits and receives the electric power by use of electromagnetic coupling in a non-contact manner. When the endoscope connector 18 of the endoscope 10 is attached to the processor device connector 12 of the endoscope processor device 11, the power feeding unit 62 and the power receiving unit 36 are arranged close to each other at a distance capable of the electromagnetic coupling, which sets a state capable of power transmission from the power feeding unit 62 to the power receiving unit 36 in a non-contact manner. The power feeding unit 62 is connected with a commercial power source 100 external to the endoscope processor device 11 via a stabilized power supply controlling unit 63. The electric power which has been supplied from the commercial power source 100 and been stabilized by the stabilized power supply controlling unit 63 is supplied to the power feeding unit 62. The electric power, which has been supplied from the stabilized power supply controlling unit 63 to the power feeding unit 62, is fed from the power feeding unit 62 to the power receiving unit 36 in a non-contact manner. The power receiving unit 36 receives the electric power from the power feeding unit 62 in a non-contact manner.

It is preferable that the power feeding unit 62 is a primary coil connected to the power source 100 and the power receiving unit 36 is a secondary coil electromagnetically coupled to the primary coil. Examples of a structure of the primary coil and the secondary coil can include a structure which has a substrate having a plane and a coil spirally wound on the plane.

The embodiment shows the example in which the power feeding unit 62 is the primary coil and the power receiving unit 36 is the secondary coil as the non-contact power supply device, but any system may be used so long as it is a device which transmits and receives the electric power in a non-contact manner.

Here, the electromagnetic coupling means that a state is being obtained where a magnetic field generated when a current flows in one (primary coil) of two coils is used to allow the electric power to be sent to the other coil (secondary coil).

Further, the endoscope 10 is provided with a power source generating unit 32 connected with the power receiving unit 36, and the power source generating unit 32 can supply the electric power to the internal circuit including an imaging unit 30 or the like. For example, the power source generating unit 32, to which the current induced to the power receiving unit 36 is input, generates from the input current a control power source which is to be supplied to the internal circuit including the imaging unit 30 and a CPU (Central Processing Unit) 46 described later. The power source generating unit 32 has, for example, a capacitor which is charged using the current induced to the power receiving unit 36 and a voltage stabilizing circuit which generates a desired voltage from a voltage charging the capacitor.

The endoscope 10 has the imaging unit 30 arranged in the distal end part 14. The imaging unit 30 is a device that converts the optical image of the observed site, which has been formed by the objective optical system after taken in from the observation window as described above, into the electrical signal and outputs the converted electrical signal as the image signal. Examples of the imaging unit 30 can include a solid-state imaging device such as a CCD (Charge Coupled Device) image sensor, and a CMOS (Complementary Metal Oxide Semiconductor) image sensor.

In the embodiment, the image signal is transmitted and received between the endoscope 10 and the endoscope processor device 11 by a non-contact type optical communication device. The image signal output from the imaging unit 30 is transmitted by way of non-contact optical transmission from the endoscope 10 via the endoscope connector 18 and the processor device connector 12 to the endoscope processor device 11. In the embodiment, in order to process the image signal from the imaging unit 30, an A/D converter (Analog/Digital converter) 34, a DSP (Digital Signal Processor) 38, a timing signal generator (TSG) 44 and the like are provided. The image signal from the imaging unit 30 is converted from an analog signal to a digital signal by the A/D converter 34. The image signal output from the A/D converter 34 is transmitted to the DSP 38. The DSP 38 subjects the image signal from the A/D converter 34 to required processes such as amplification, gamma correction, and white balance processing.

In order for the non-contact optical transmission between the endoscope 10 and the endoscope processor device 11, the following configuration is provided, for example. The endoscope 10 is provided with an endoscope-side digital interface (DI) 40 connected with the DSP 38, and an image signal transmitting unit 42 connected with the endoscope-side DI 40. The image signal processed by the DSP 38 is transmitted via the endoscope-side DI 40 to the image signal transmitting unit 42. The image signal from the imaging unit 30 is subjected to the processes, and, depending on the processed image signal, the optical signal is transmitted from the image signal transmitting unit 42 toward the endoscope processor device 11. The image signal transmitting unit 42 may be a light emitting device capable of emitting a light for the optical communication, and examples thereof can include a laser emitting element, a light emitting diode, and the like, for example. The laser emitting element is an element that emits a laser light which is a coherent light, and examples of laser can include a gas laser, a solid-state laser, a semiconductor laser, and the like.

The endoscope connector 18 of the endoscope 10 has arranged therein at least the image signal transmitting unit 42. Other devices such as the endoscope-side DI 40 may be arranged in the endoscope connector 18 of the endoscope 10.

The endoscope processor device 11 is provided with an image signal receiving unit 64 which receives the optical signal from the image signal transmitting unit 42, a processor device-side DI 70 connected with the image signal receiving unit 64, and a signal processing circuit 72 connected with the processor device-side DI 70. The image signal receiving unit 64 is a light receiving device that converts the received optical signal into the electrical signal, and examples thereof can include a light receiving element composed of a semiconductor device such as a photodiode and a phototransistor. The electrical signal from the image signal receiving unit 64 is passed through the processor device-side DI 70, subjected to an analog process by the signal processing circuit 72 and output to the monitor 19.

In the embodiment, the image signal transmitting unit 42 and the image signal receiving unit 64 constitute an image signal transceiving device by means of non-contact optical communication. The non-contact optical communication (optical wireless communication system) which transmits and receives the signal using an infrared light or the like can be used as the image signal transmitting unit 42 which transmits the image signal from the imaging unit 30 in a non-contact manner and the image signal receiving unit 64 which receives the signal from the image signal transmitting unit 42 in a non-contact manner.

When the endoscope connector 18 of the endoscope 10 is attached to the processor device connector 12 of the endoscope processor device 11, the image signal transmitting unit 42 and the image signal receiving unit 64 are arranged close to each other at a distance capable of the optical communication, which sets a state capable of the optical communication from the image signal transmitting unit 42 to the image signal receiving unit 64 in a non-contact manner.

The control signal is transmitted and received between the endoscope 10 and the endoscope processor device 11 by way of the non-contact type optical communication. The imaging unit 30 is connected with the TSG 44 and CPU 46 for controlling the imaging unit 30. The TSG 44 and the CPU 46 output to the imaging unit 30 a drive signal in order for the imaging unit 30 to acquire the image signal. The CPU 46 is connected with an endoscope-side communication interface (CI) 48 and an endoscope-side signal transceiving unit 50. The endoscope-side signal transceiving unit 50, which is a device capable of optically transmitting and receiving non-contactually the control signal between the endoscope 10 and the endoscope processor device 11, is provided with a light emitting device which optically transmits the control signal as the optical signal to the endoscope processor device 11 and a light receiving device which receives as the optical signal the control signal from the endoscope processor device 11. As the endoscope-side signal transceiving unit 50, there can be used, for example, non-contact optical data communication means by means of IrDA (Infrared Data Association) communication which includes an infrared light emitting element for optically (infrared light) transmitting the signal and a light receiving element (photodiode, phototransistor or the like) for optically receiving the signal. The endoscope connector 18 of the endoscope 10 has arranged therein at least the endoscope-side signal transceiving unit 50. Other devices such as the endoscope-side CI 48 and the like may be arranged in the endoscope connector 18 of the endoscope 10.

The endoscope processor device 11 is provided with a processor device-side signal transceiving unit 66 which optically transmits and receives non-contactually the control signal to and from the endoscope-side signal transceiving unit 50 of the endoscope 10, and a processor device-side CI 74 which is connected with the processor device-side signal transceiving unit 66. The processor device-side signal transceiving unit 66, which is a device capable of optically transmitting and receiving non-contactually the control signal between the endoscope 10 and the endoscope processor device 11, is provided with a light emitting device which optically transmits the control signal as the optical signal to the endoscope 10 and a light receiving device which receives as the optical signal the control signal from the endoscope 10. As the processor device-side signal transceiving unit 66, there can be used, for example, non-contact optical data communication means by means of IrDA (Infrared Data Association) which includes an infrared light emitting element, which is separately provided from that for the endoscope-side signal transceiving unit 50, for optically (infrared light) transmitting the signal, and a light receiving element (photodiode, phototransistor or the like), which is separately provided from that for endoscope-side signal transceiving unit 50, for optically receiving the signal. The infrared light generally refers to an electromagnetic wave having a wavelength of 0.7 μm to 1 mm.

When the endoscope connector 18 of the endoscope 10 is attached to the processor device connector 12 of the endoscope processor device 11, the endoscope-side signal transceiving unit 50 and the processor device-side signal transceiving unit 66 are arranged close to each other at a distance capable of the optical communication, which sets a state capable of the optical transmission and reception in a non-contact manner between the endoscope-side signal transceiving unit 50 and the processor device-side signal transceiving unit 66.

Both the endoscope-side signal transceiving unit 50 which transceives in a non-contact manner the control signal for controlling the imaging unit 30, and the processor device-side signal transceiving unit 66 which transceives in a non-contact manner the control signal from the endoscope-side signal transceiving unit 50, can use a wireless communication system and a magnetic communication system, without limitation to the non-contact optical communication (optical wireless communication system).

The endoscope processor device 11 is provided with a light source 68. Examples of the light source 68 can include a xenon lamp and a semiconductor device such as a laser diode and a light emitting diode. The endoscope 10 is provided with a light guide 52. An end of the light guide 52 is provided with the light guide bar 20 continuously connected with the light guide. The light guide bar 20 is projected from the endoscope connector 18 and connected with the processor device connector 12 of the endoscope processor device 11. The light source 68 is positioned to align with the light guide bar 20, such that the light from the light source 68 is transmitted via the light guide bar 20 and the light guide 52 to the distal end part 14.

The endoscope processor device 11 is provided with a controlling unit 76, and the controlling unit 76 controls the processor device-side DI 70 and the like constituting the internal circuit in the endoscope processor device 11 and the light source 68. In addition, the controlling unit 76 transmits the control signal to the CPU 46 and the like constituting the internal circuit in the endoscope 10 to control entirely the endoscope system 2. For example, the endoscope processor device 11 is provided with an input device 80 (such as an operation switch, a keyboard, or the like).

A user uses the input device 80 to input an instruction for ON/OFF of the power source of the endoscope processor device 11. The control signal based on the input instruction is transmitted from the controlling unit 76 in the endoscope processor device 11 to the CPU 46 in the endoscope 10 via a non-contact type optical communication device which is constituted by the processor device-side signal transceiving unit 66 and the endoscope-side signal transceiving unit 50.

The control signal from the CPU 46 is also transmitted to the controlling unit 76 in the endoscope processor device 11 via the non-contact type optical communication device which is constituted by the processor device-side signal transceiving unit 66 and the endoscope-side signal transceiving unit 50.

Figure 3:
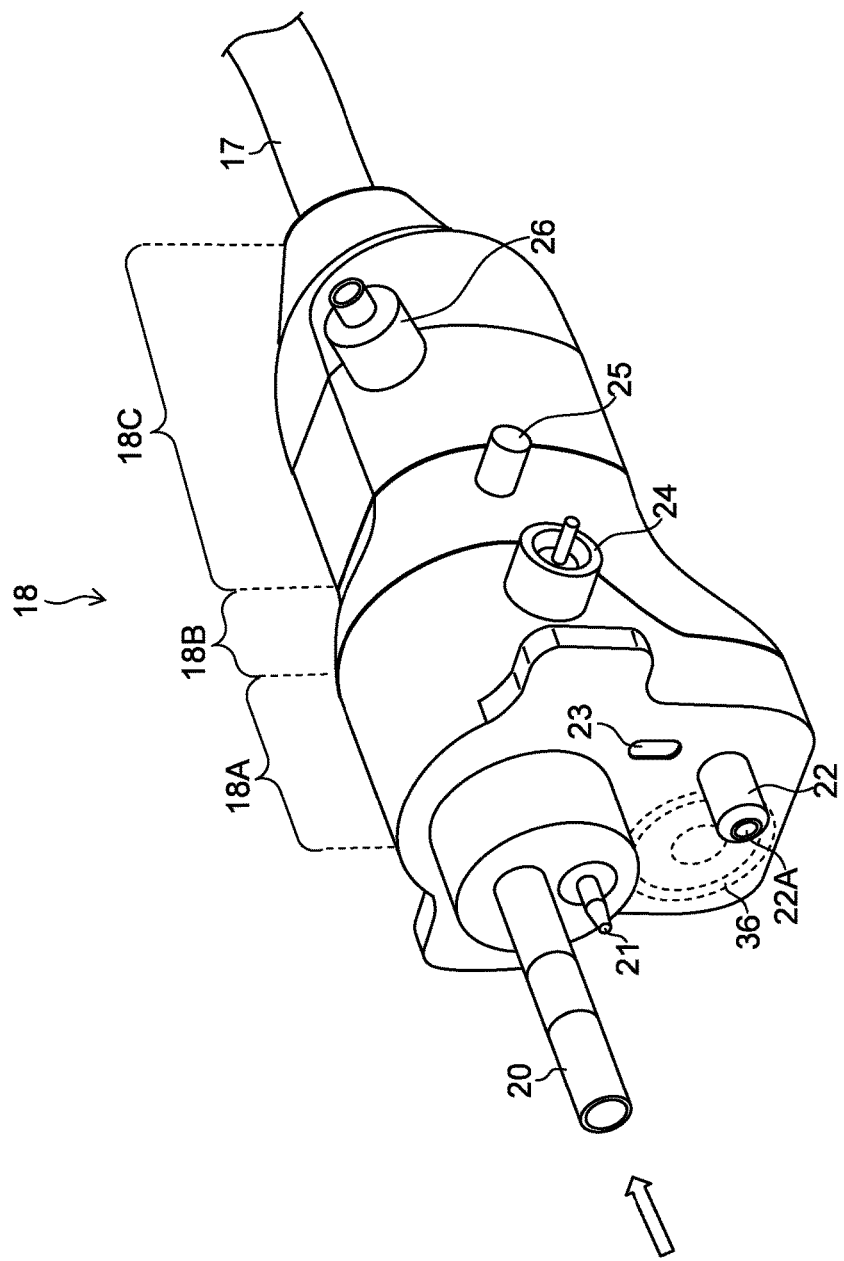
FIG. 3 is an outer appearance view of an endoscope connector of an endoscope.

FIG. 3 is an outer appearance view of the endoscope connector 18. As described above, the endoscope 10 and the endoscope processor device 11 perform the reception and feed of the electric power in a non-contact manner, the transmission and reception of the image signal, and the bidirectional transmission and reception of the control signal. The endoscope connector 18 does not need to be provided with an electric contact which is directly connected with the endoscope processor device 11. Therefore, the endoscope connector 18 can have a watertight structure by being covered by a resin which has electrical insulating property and is excellent in chemical resistance, for example. The endoscope connector 18 having the watertight structure allows electrical parts or the like inside the endoscope connector 18 to be protected from cleaning water or the like and eliminates the need for attaching a watertight cap that is a separate body when cleaning and sterilizing.

As shown in the figure, the endoscope connector 18 is provided with the light guide bar 20 and an image signal transmitting connector 22 which project from the endoscope connector 18 toward the processor device connector 12 (not shown).

The endoscope connector 18 can include a first connector case 18A, a second connector case 18B, and a third connector case 18C in an order of being connected with the processor device connector 12 of the endoscope processor device 11, for example.

The light guide bar 20 projects from the first connector case 18A having a connection face with the processor device connector 12 toward the processor device connector 12 (in an inserting direction). An air sending pipe sleeve 21 is provided below the light guide bar 20 substantially in parallel to the light guide bar 20. The air sending pipe sleeve 21 is in communication with an air and water feed conduit which is provided in the endoscope 10 for feeding the air and water to the distal end part 14 of the endoscope 10.

The image signal transmitting connector 22 projects along the inserting direction from the connection face of the first connector case 18A to the processor device connector 12. The image signal transmitting connector 22 is used for positioning to align the image signal transmitting unit 42 of the endoscope 10 with the image signal receiving unit 64 of the endoscope processor device 11. Particularly, the image signal transmitting unit 42 is arranged in a direction extending a central axis of the image signal transmitting connector 22. A window 22A through which a light is transmitted is provided at a tip end of the image signal transmitting connector 22. The signal passes through the window 22A such that the image signal communication is optically transmitted and received in a non-contact manner between the image signal transmitting unit 42 and the image signal receiving unit 64.

The connection face of the first connector case 18A is also provided with a window 23 at a position corresponding to the endoscope-side signal transceiving unit 50. Through the window 23, signal communication control is optically transmitted and received in a non-contact manner between the endoscope-side signal transceiving unit 50 and the processor device-side signal transceiving unit 66.

The power receiving unit 36 is arranged at a position which is inside the first connector case 18A and closer to the connection face of the first connector case 18A. The power receiving unit 36 is arranged inside the first connector case 18A such that the power receiving unit 36 is not exposed externally.

The first connector case 18A has an air and water feeding connector 24 arranged on a lateral side. The air and water feeding connector 24 is connected to a water sending tank (not shown). The air and water feeding button on the operating portion 15 can be operated to feed air or water to the distal end part 14. The water fed to the distal end part 14 removes dirt on a lens surface of the distal end part 14. The air fed to the distal end part 14 expands a lumen of the patient or removes water droplets on the lens.

A suction connector (not shown) is arranged on a lateral side opposite to the air and water feeding connector 24 of the first connector case 18A. By connecting a tube with the suction connector, communication with a suction device not shown in the figure can be established. A suction button on the operating portion 15 is operated in a state where the suction device is driven such that a lesioned part or the like can be suctioned from a forceps opening of the distal end part 14.

In the embodiment, the suction connector is provided on a lateral side opposite to the image signal transmitting unit 42 with the endoscope connector 18 being seen from the inserting direction (seen from an arrow direction in the figure). In other words, the suction connector is arranged on the lateral side farther from the image signal transmitting connector 22. This configuration can prevent the window 22A of the image signal transmitting connector 22 from becoming dirty, even in a case where a lesioned part goes out from the suction connector when detaching the tube from the suction connector, for example. On the other hand, since the suction connector is arranged on the lateral side closer to the power receiving unit 36, a lesioned part from the suction connector may adhere thereto. An area on the endoscope connector 18 where the power receiving unit 36 is arranged is composed of a plane, which allows cleaning such as wiping to be easily done.

The second connector case 18B has a balloon connector 25 arranged on a lateral side. By connecting a tube with the balloon connector 25, a balloon (not shown) provided in the insertion portion 13 can be expanded and contracted. In a case of the endoscope 10 which does not have the balloon in the insertion portion 13, the endoscope connector 18 does not need to have the balloon connector 25 arranged thereon.

The second connector case 18B has a sub-water feeding connector (not shown) arranged on a lateral side opposite to the balloon connector 25. By connecting a tube with the sub-water feeding connector, the water can be fed to the distal end part 14 of the endoscope 10. The water fed via the sub-water feeding connector to the distal end part 14 rinses off dirt adhered to the body cavity, bleeding owing to endoscope manipulation, or the like.

The third connector case 18C has a venting connector 26 arranged on a lateral side. The venting connector 26 is used for a leak test which checks air leakage of the insertion portion 13. The venting connector 26 is in communication with the inside of the endoscope connector 18. The inside of the endoscope connector 18 is in communication with respectively the insides of the universal cord 17, the operating portion 15, and the insertion portion 13, and thus, the venting connector 26 is in communication with the inside of the insertion portion 13.

The universal cord 17 projects from an end part of the third connector case 18C.

Figure 4:
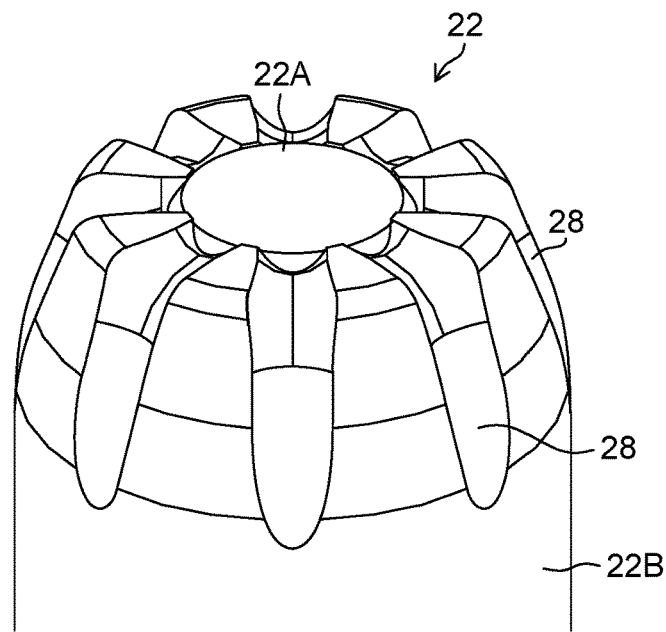
FIG. 4 is a perspective view showing a shape of an a tip end of an image signal transmitting connector.
Figure 5:
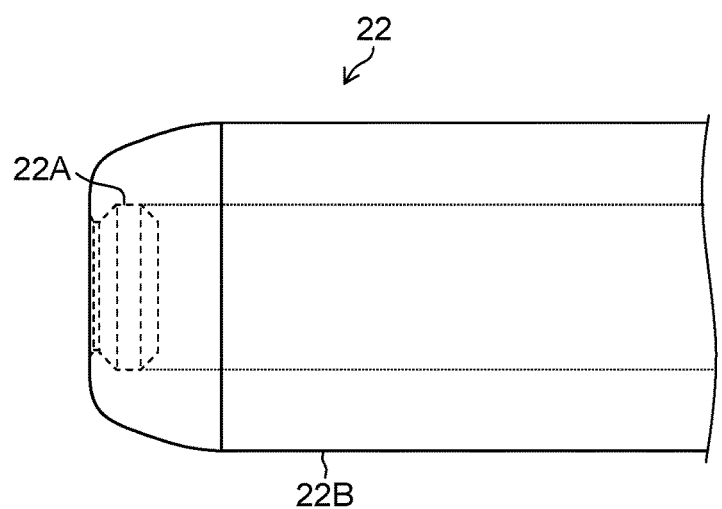
FIG. 5 is a lateral view showing the shape of the tip end of the image signal transmitting connector shown in FIG. 4.

Next, a description is given of a shape of the tip end of the image signal transmitting connector 22. FIG. 4 is a perspective view showing the shape of the tip end of the image signal transmitting connector 22, and FIG. 5 is a lateral view showing the shape of the tip end of the image signal transmitting connector 22 shown in FIG. 4. In FIG. 5, grooves are omitted for the purpose of easy understanding of the shape of the tip end of the image signal transmitting connector. The same holds for FIG. 7 and FIG. 8.

The image signal transmitting connector 22 has the window 22A whose tip end is formed of a glass member for transmitting the image signal as described above, and a circumference of the window 22A is formed of a guide member 22B.

As shown in FIG. 4, in the present embodiment, in the tip end of the image signal transmitting connector 22, the guide member 22B has grooves 28 thereon radially extending from the window 22A. By providing the grooves 28, capillarity owing to surface tension acting on between the grooves 28 and the water droplets can eliminate the water droplets adhered to the window 22A. Therefore, it is possible to prevent the laser efficiency decrease caused by water droplets adhered to the window 22.

As for a positions where the grooves 28 are to be formed, it is preferable that the grooves are at least in a gravitational direction with respect to a position of the endoscope connector in cleaning and sterilizing. The grooves arranged in the gravitational direction allow water droplets which have been adhered to the window 22A to be easily eliminated by gravity after cleaning and sterilizing. Even if the grooves 28 are not formed in the gravitational direction, water droplets can be eliminated from the window 22A by the capillarity.

It is preferable that the grooves 28 are formed, as shown in FIG. 4, from the window 22A in eight directions at equal intervals between the grooves. In engaging the image signal transmitting connector 22 with the endoscope connector 18, a screw structure may be used for engagement in some cases. The groove 28 formed in eight directions allows any of the grooves to be arranged to have a component of the gravitational direction. The grooves 28 are formed in eight directions in FIG. 4, but any of the grooves can be arranged in the gravitational direction by forming in four directions. It is preferable that the number of the grooves is from four to eight in terms of the directions thereof.

As shown in FIG. 5, the window 22A can be arranged in a state of retracting inward from the tip end of the image signal transmitting connector 22, that is, the window 22A can be arranged so as to be concave. Such a configuration can prevent that a foreign object comes into contact with the window 22A to damage the window 22A. A concave amount of the window 22A is preferably in a range equal to or less than 0.3 mm, and more preferably in a range equal to or less than 0.1 mm. A lower limit of the concave amount is preferably 0.05 mm or more.

When the window 22A made to be concave from the tip end of the image signal transmitting connector 22, it can be also considered that a level difference is formed at a border between the window 22A and the guide member 22B such that the water droplets become less likely to move. However, according to the embodiment, by arranging the grooves 28 on the guide member 22B, the water droplets can be made to move from the window 22A toward the guide member 22B and be easily eliminated. Therefore, the water droplets can be made to move even if there is such a level difference, and it is possible to prevent the water droplets and the water scale from adhering to the window 22A.

Figure 6:
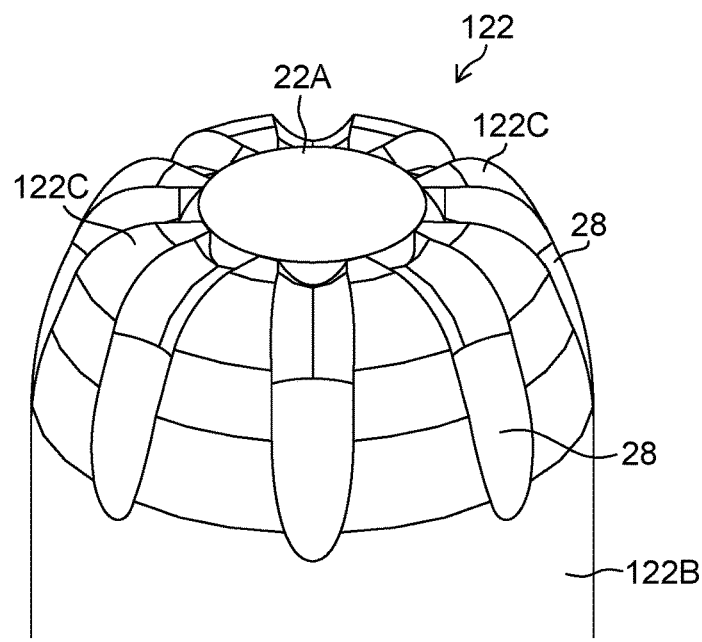
FIG. 6 is a perspective view showing a shape of a tip end of an image signal transmitting connector according to another embodiment.
Figure 7:
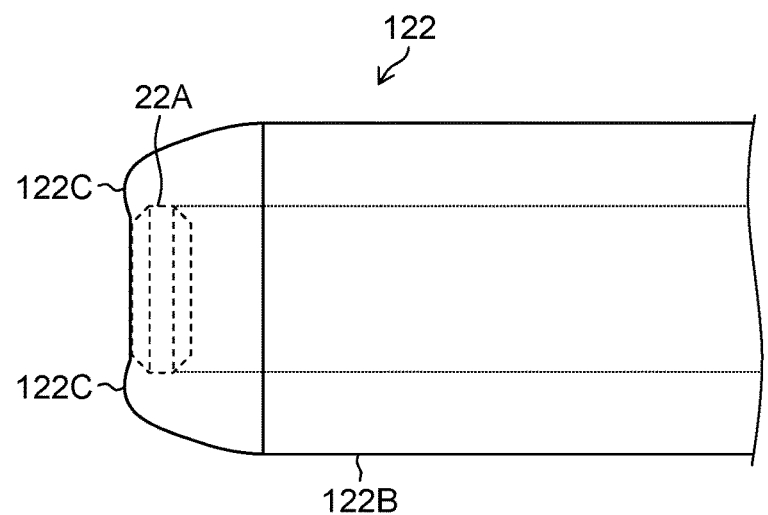
FIG. 7 is a lateral view showing the shape of the tip end of the image signal transmitting connector shown in FIG. 6.

FIG. 6 is a perspective view showing a shape of a tip end of an image signal transmitting connector 122 according to another embodiment, and FIG. 7 is a lateral view showing the shape of the tip end of the image signal transmitting connector 122 shown in FIG. 6.

The image signal transmitting connector 122 shown in FIGS. 6 and 7 is different in having curved convex shapes 122C at a tip end of a guide member 122B from the image signal transmitting connector 22 shown in FIGS. 4 and 5. By providing the curved convex shapes 122C at the tip end of the guide member 122B, even if the tip end of the image signal transmitting connector 122 comes into contact with a foreign object, the foreign object contacts with the convex shape 122C so as to prevent the foreign object from coming into contact with the window 22A. Therefore, the window 22A can be prevented from being damaged.

In this way, because the curved convex shapes 122C arranged on the tip end of the image signal transmitting connector 122 can prevent the window 22A from being damaged, the tip end of the image signal transmitting connector 122 can have a configuration without a level difference between the window 22A and the guide member 122B. Since the level difference is not provided, when wiping the window 22A, a wiping article of gauze or the like can be prevented from being caught on the guide member 122B. Therefore, the window can be efficiently wiped.

Figure 8:
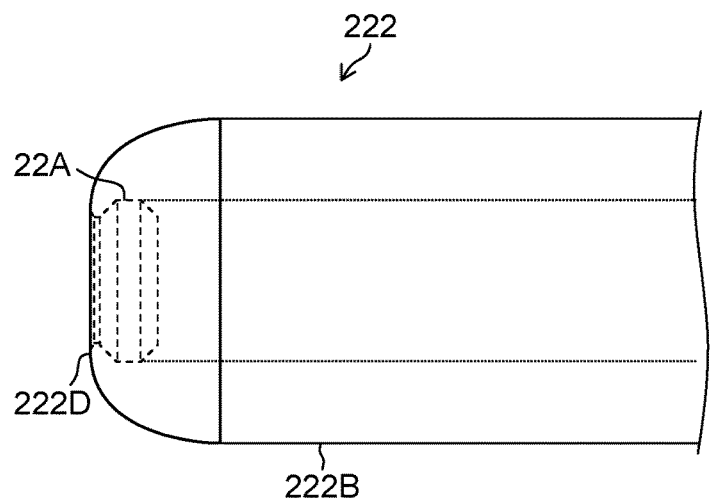
FIG. 8 is a lateral view showing an image signal transmitting connector according to still another embodiment.

FIG. 8 is a lateral view showing an image signal transmitting connector 222 according to still another embodiment. As shown in FIG. 8, in the embodiment, a tip end of the image signal transmitting connector 222 is round-chamfered (R chamfered) from a tip end 222D of a guide member 222B toward its circumference. By round-chamfering the tip end 222D of the guide member 222B of the image signal transmitting connector 222 from the tip end 222D toward its circumference, a inflection point can be eliminated between the tip end and its lateral portion of the image signal transmitting connector 222. Therefore, it is possible to make water droplets which has been adhered to the window 22A be likely moved by gravity. In the present invention, the "round chamfering" refers to a structure having a curved surface shape from the tip end of the guide member toward the lateral surface, and a shape circumscribing the tip end surface and the lateral surface may be a partial circle (a part of a circle) or a partial ellipse (a part of an ellipse).

An image transmitting connector of related art has a guide member with a tapered shape in order to ensure its insertability. However, in the guide member having a tapered shape, because the inflection point is present at a position where the tapered portion begins viewing from the tip end, the water droplets easily stop at this inflection point due to the pinning effect of wetting. The guide member round-chamfered can make the water droplets adhered to the window to be likely to move.

Figure 9:
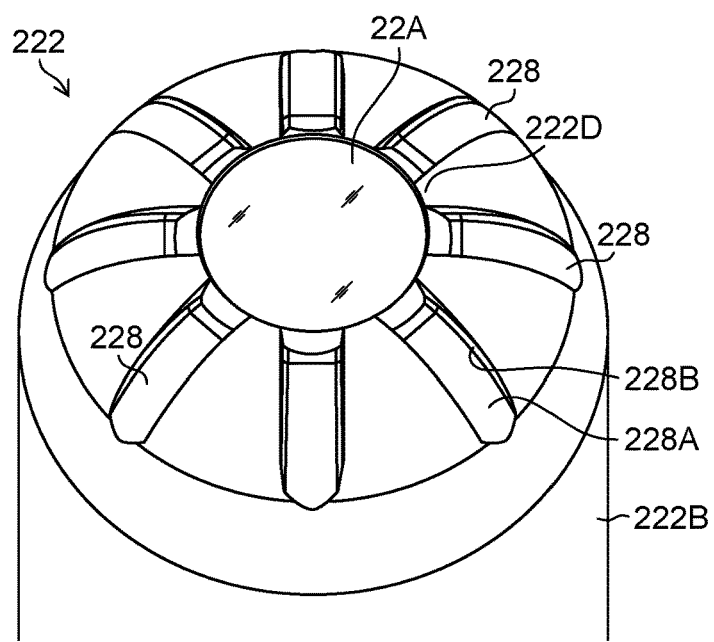
FIG. 9 is a perspective view showing the shape of the tip end of the image signal transmitting connector shown in FIG. 8.
Figure 10:
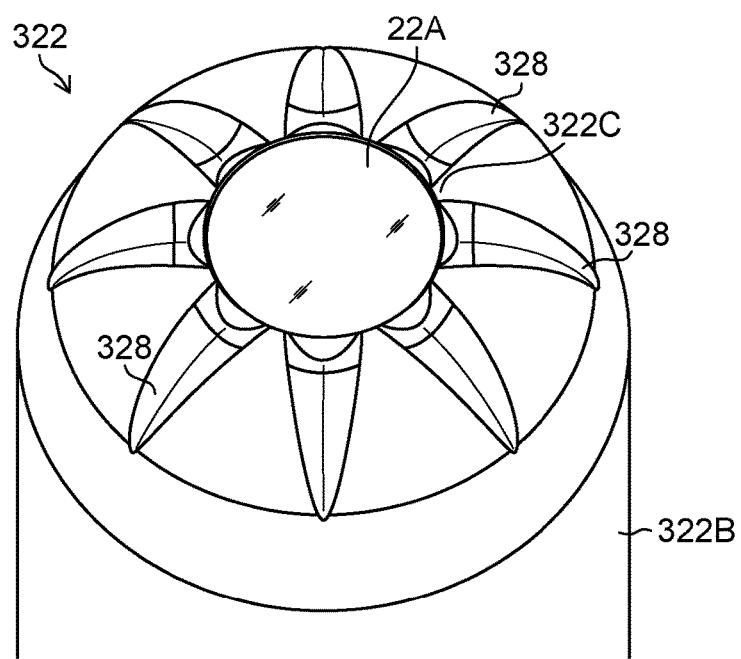
FIG. 10 is a perspective view showing a shape of a tip end of an image signal transmitting connector according to still another embodiment.

FIG. 9 is a perspective view showing the shape of the tip end of the image signal transmitting connector 222 shown in FIG. 8, and FIG. 10 is a perspective view showing a shape of a tip end of the image signal transmitting connector 322 according to still another embodiment. By use of FIGS. 9 and 10, a description is given of a shape of the grooves. As for the shape of the grooves, as shown in FIG. 9, grooves 228 may be formed to have the same width from the tip end of the image signal transmitting connector 222 toward its circumference. As shown in FIG. 10, grooves 328 may be formed to each have a width becoming narrower toward the circumference of the image signal transmitting connector 322. Any of the shapes may be used to lead the water droplets to the grooves.

It is preferable that the grooves 228 or 328 have a volume enough to collect water droplets remaining on a grass surface of the window 22A. It is preferable that, in the shape of the groove 228 or 328 for example, a corner between a bottom surface 228A and lateral surface 228B of the grooves 228 is C chamfered (chamfered plane) or round chamfered. By C chamfering or round chamfering the corner, dirt such as water scale which has been accumulated because water droplets led to the grooves 228 are dried, can be easily removed. C chamfering the corner refers to chamfering with a straight line the bottom surface 228A and lateral surface 228B of the groove 228. Round chamfering the corner refers to, similarly in the case of C chamfering the guide member 222B, a structure having a curved surface shape from the bottom surface 228A of the groove 228 toward the lateral surface 228B. A shape circumscribing the bottom surface 228A and the lateral surface 228B may be a partial circle (a part of a circle) or a partial ellipse (a part of an ellipse). The shape of the groove is not limited to the shape shown in FIG. 9 or FIG. 10 so long as it can lead the water droplets adhered to the window 22A to the grooves. The description is given of the configuration in which the tip end of the guide member is round chamfered in FIGS. 9 and 10, but the chamfered configuration can be applied also to the image signal transmitting connector shown in FIGS. 4 and 6.

It is preferable that the grass surface of the window 22A is subjected to a process for lowering an adhering force of water. By subjecting the glass surface to the process for lowering the adhering force of water, water droplets adhered to the glass surface can be likely moved from the glass surface to the guide member 22B. The level difference is formed at a border between the window 22A and the guide member 22B as described above. By subjecting the glass surface to the process for lowering the adhering force of water, the water droplets can be likely moved to a metal surface of the guide member 22B.

Examples of the processes for lowering the adhering force of water on the glass surface can include subjecting the glass surface to fluorine coating. Fluorine coating may be performed by a known method. In addition, when sapphire glass is used as a material for the glass member of the window 22A, it is possible to make water droplets be likely moved from the glass surface of the glass member.

The adhering force of water on the glass surface may be sufficient if it can be lowered than the adhering force of water on the metal composing the guide member. If the adhering force of water on the glass surface can be lowered than that on the metal composing the guide member, water droplets adhered to the glass surface can be moved to the guide member.

What is claimed is:

1. An endoscope connector comprising:
a light emitting device which transmits an image signal to an endoscope processor device via optical communication; and
an image signal transmitting connector which is connected with a processor device connector of the endoscope processor device,
wherein the endoscope connector is connected with the processor device connector, and the light emitting device is arranged in the image signal transmitting connector,
wherein the image signal transmitting connector includes:
a glass member which is provided at a tip end of the image signal transmitting connector, wherein the image signal passes through the glass member; and
a guide member formed on a circumference of the glass member,
wherein the guide member has grooves thereon radially extending from the glass member.

2. The endoscope connector according to claim 1, wherein the glass member is concave from the tip end of the image signal transmitting connector in a range equal to or less than 0.3 mm from the guide member.

3. The endoscope connector according to claim 1, wherein the grooves are formed in four to eight directions from the glass member at equal intervals between the grooves.

4. The endoscope connector according to claim 1, wherein a corner formed by a bottom surface and lateral surface in each groove is C chamfered or round chamfered.

5. The endoscope connector according to claim 1, wherein the guide member is round chamfered from the tip end of the image signal transmitting connector toward a circumference thereof.

6. The endoscope connector according to claim 1, wherein a tip end of the guide member has a curved convex shape.

7. The endoscope connector according to claim 1, wherein the glass member has been subjected to a process for lowering adhering force of water.

8. The endoscope connector according to claim 7, wherein the process for lowering the adhering force of water is a process for subjecting the glass member to fluorine coating.

9. The endoscope connector according to claim 1, wherein a material of the glass member s sapphire glass.

10. An endoscope comprising:
an image sensor arranged at a distal end part of the endoscope;
a light guide which transmits a light to the distal end part; and
an endoscope connector,
wherein the endoscope connector comprises:
a light emitting device which transmits an image signal to an endoscope processor device via optical communication; and
an image signal transmitting connector which is connected with a processor device connector of the endoscope processor device,
wherein the endoscope connector is connected with the processor device connector, and the light emitting device is arranged in the image signal transmitting connector,
wherein the image signal transmitting connector includes:
a glass member which is provided at a tip end of the image signal transmitting connector, wherein the image signal passes through the glass member; and
a guide member formed on a circumference of the glass member, wherein the guide member has grooves thereon radially extending from the glass member.

11. An endoscope system comprising:
an endoscope; and
an endoscope processor device comprising a processor device connector,
wherein the endoscope comprises:
an imaging sensor arranged at a distal end part of the endoscope;
a light guide which transmits a light to the distal end part; and
an endoscope connector,
wherein the endoscope connector comprises:

a light emitting device which transmits an image signal to the endoscope processor device via optical communication; and an image signal transmitting connector which is connected with the processor device connector, wherein the endoscope connector is connected with the processor device connector, and the light emitting device is arranged in the image signal transmitting connector, wherein the image signal transmitting connector includes:

a glass member which is provided at a tip end of the image signal transmitting connector, wherein the image signal passes through the glass member; and a guide member formed on a circumference of the glass member, wherein the guide member has grooves thereon radially extending from the glass member.

* * * * *